United States Patent
Dadas

(10) Patent No.: US 8,685,414 B2
(45) Date of Patent: Apr. 1, 2014

(54) METHOD FOR THE TREATMENT OF INFRAORBITAL DARK CIRCLES USING BOTULINUM TOXINS

(76) Inventor: Christopher A. Dadas, Strongsville, OH (US)

( * ) Notice: Subject to any disclaimer, the term of this patent is extended or adjusted under 35 U.S.C. 154(b) by 30 days.

(21) Appl. No.: 13/290,664

(22) Filed: Nov. 7, 2011

(65) Prior Publication Data

US 2012/0115792 A1     May 10, 2012

Related U.S. Application Data

(60) Provisional application No. 61/410,480, filed on Nov. 5, 2010.

(51) Int. Cl.
*A61K 38/16*     (2006.01)
*A61Q 90/00*     (2009.01)

(52) U.S. Cl.
USPC .................................. 424/236.1; 424/247.1

(58) Field of Classification Search
None
See application file for complete search history.

(56) References Cited

PUBLICATIONS

Dayan et al., Facial Plast Surg Clin N Am, 11:349-358, 2003.*
Spiegel et al., Plast and Reconstruct Surg, 116:1937-1942, Dec. 2005.*
Atamoros FP, P2403, Topical Botulinum Toxin Type A for the Treatment of Moderate to Severe Lateral Canthal Lines: Preliminary Safety and Efficacy Results of a Blinded, Randomized, Placebo Controlled Trial, American Academy of Dermatology meeting, Aug. 2009. Retrieved online: <http://www.revance.com/news/publications.html> Retrieved on Jan. 29, 2013.*
Sadick et al., J of Cosmetic Derm, 6: 218-222, 2007.*
Glaser et al., J Drugs in Derm, 9(8): s118-s128, Aug. 2010.*
Alam et al., Arch Dermatol., 138:1180-1185, Sep. 2002.*
Klein AW, Dermatol Clin., 22:145-149, 2004.*
Liquid Face Lift Association website, published online May 25, 2009. Retrieved from: http://web.archive.org/web/2009525142307/http://www.liquidfacelift.com/nose_area_wrinkles.asp> Retrieved on: Jul. 5, 2013.*

* cited by examiner

*Primary Examiner* — Daniel E Kolker
*Assistant Examiner* — Stacey N MacFarlane
(74) *Attorney, Agent, or Firm* — Brigitte C. Phan; Ted Chan; Debra Condino

(57) ABSTRACT

Infraorbital dark circles can be treated by administration of a botulinum toxin to a patient. The botulinum toxin can be botulinum toxin type A and the botulinum toxin can be administered to or to the vicinity of an eye of a patient with infraorbital dark circles.

7 Claims, 1 Drawing Sheet

METHOD FOR THE TREATMENT OF INFRAORBITAL DARK CIRCLES USING BOTULINUM TOXINS

CROSS REFERENCE

This application claims the benefit of U.S. provisional patent application No. 61/410,480, filed Nov. 5, 2010, the entire disclosure of which is incorporated herein by reference.

FIELD

Embodiments of the present invention relate to methods for treating infraorbital dark circles with botulinum toxins.

BACKGROUND

Skin is composed of the epidermis and the dermis. Below these layers lies the hypodermis, which is not usually classified as a layer of skin. The hypodermis is also commonly referred to as subcutaneous fat layer, or subcutaneous tissue. The outermost epidermis is made up of stratified squamous epithelium with an underlying basement membrane. It contains no blood vessels, and is nourished by diffusion from the dermis. The main type of cells which make up the epidermis are keratinocytes, with melanocytes and langerhans cells also present. This layer of skin is responsible for keeping water in the body and keeping other harmful chemicals and pathogens out.

The dermis lies below the epidermis and contains a number of structures including blood vessels, nerves, hair follicles, smooth muscle, glands and lymphatic tissue. The dermis (or corium) is typically 3-5 mm thick and is the major component of human skin. It is composed of a network of connective tissue, predominantly collagen fibrils providing support and elastic tissue providing flexibility. The main cell types are fibroblasts, adipocytes (fat storage) and macrophages. The hypodermis lies below the dermis. Its purpose is to attach the skin to underlying bone and muscle as well as supplying it with blood vessels and nerves. It is made up of loose connective tissue and elastin. The main cell types are fibroblasts, macrophages and adipocytes. The hypodermis contains 50% of body's fat, which serves as padding and insulation for the body. Hyaluronic acid (HA) is a part of the dermis composition and is a major component of the extra cellular matrix.

Infraorbital dark circles are a common condition that presents as a bilateral semicircle of hyperchromatic discoloration of the skin. The dark discoloration may be seen both superior and inferior to the eyelids in a semicircle shape following the orbital rim. The discoloration may extend beyond the orbital rim on both the medial and lateral sides of the eyelid opening. These dark semicircles can be a significant cosmetic problem for men and women of all ages, causing misperceptions of advanced age, sadness, tiredness, or the appearance of a hangover. This unpleasant appearance can have a significant impact on an individual's emotional well being, productivity at work or school, and overall quality of life. The presence of these dark circles may also have a negative impact on employment for individuals who rely on a positive appearance to maintain a career or develop future business.

Numerous contributing factors have been identified in the development of infraorbital dark circles, and multiple causes of the condition may be present in any one case. The very thin dermal layer beneath the eye plays an important role. Other factors that may contribute to the darkening appearance include congestion within the microvascular and subcutaneous blood vessel plexus, postinflammatory hyperpigmentation, dermal melanin deposition, allergic dermatitis, and shadowing due to edema or wrinkles. The available treatments for infraorbital dark circles, including topical creams, lotions, oils, vitamins and makeup, have limited efficacy.

Botulinum neurotoxins (BoNTs) such as, for example, BoNT/A, BoNT/B, etc., act on the nervous system by blocking the release of neurosecretory substances such as neurotransmitters. The action of BoNT is initiated by its binding to a receptor molecule on the cell surface, then the toxin-receptor complex undergoes endocytosis. Once inside the cell, BoNT cleaves exocytotic specific proteins responsible for neurotransmitter docking and release from the cell known as the SNARE proteins (soluble N-ethylmaleimide-sensitive factor attachment protein receptor). The resulting transient chemodenervation has been utilized medically to block motor neurotransmission at the neuromuscular junction leading to a variety of therapeutic applications.

DESCRIPTION OF EXEMPLARY EMBODIMENTS

Figure 1:
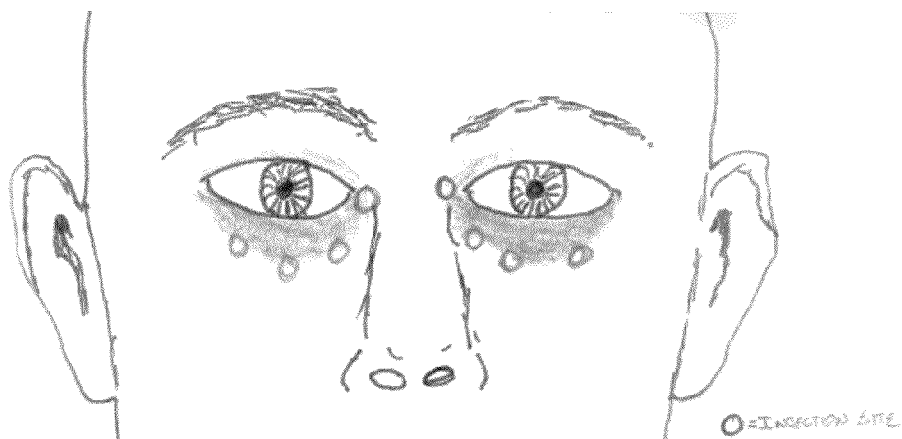
FIG. 1 depicts the injection protocol used in Example 1, wherein four (4) discrete injection sites are employed inside the orbital rim for each eye, beginning on the eye's inner edge and extending along the bottom edge toward the outer edge.

Botulinum neurotoxins are able to change local vascular perfusion by their action on neurosecretory substances such as, but not limited to, acetylcholine (ACh), calcitonin gene related peptide (cGRP), substance P (SP), glutamate, and norepinephrine. Botulinum toxin's vasoactive effect can be utilized to enhance blood flow, lymphatic drainage, and extravascular perfusion in the orbital region. This can decrease the pooling of blood and extravascular fluid in the infraorbital region, thereby counteracting several of the known causes of infraorbital discoloration, resulting in a refreshed appearance.

The following definitions are provided and apply herein.

"Affected skin area" means the area to be treated, for example, an area of skin at or near an area of skin with darker skin color.

"Heavy chain" means the heavy chain of a botulinum neurotoxin. It preferably has a molecular weight of about 100 kDa and may be referred to herein as H chain or as H.

"$H_N$" means a fragment (preferably having a molecular weight of about 50 kDa) derived from the H chain of a botulinum neurotoxin which is approximately equivalent to the amino terminal segment of the H chain, or the portion corresponding to that fragment in the intact in the H chain. It is believed to contain the portion of the natural or wild type botulinum neurotoxin involved in the translocation of the L chain across an intracellular endosomal membrane.

"$H_C$" means a fragment (about 50 kDa) derived from the H chain of a botulinum neurotoxin which is approximately equivalent to the carboxyl terminal segment of the H chain, or the portion corresponding to that fragment in the intact H chain. It is believed to be immunogenic and to contain the portion of the natural or wild type botulinum neurotoxin involved in high affinity, pre-synaptic binding to motor neurons.

"Light chain" means the light chain of a botulinum neurotoxin. It preferably has a molecular weight of about 50 kDa, and can be referred to as L chain, L or as the proteolytic domain (amino acid sequence) of a botulinum neurotoxin. The light chain is believed to be effective as an inhibitor of neurotransmitter release when it is released into a cytoplasm of a target cell.

"Neurotoxin" means a chemical entity that is capable of interfering with the functions of a neuron. For example, a neurotoxin may interfere with the transmission of an electrical signal from a nerve cell to its target. The target may be, for example, another nerve cell, a tissue or an organ. The "neurotoxin" may be naturally occurring or other.

"Variant" means a chemical entity which is slightly different from a parent chemical entity but which still has a biological effect similar, or substantially similar to the biological effect of the chemical entity. The biological effect of the variant may be substantially the same or better than that of the parent. For example, a variant neurotoxin component may have one or more amino acid substitutions, amino acid modifications, amino acid deletions and/or amino acid additions. An amino acid substitution may be conservative or non-conservative, as is well understood in the art. In addition, variants of neurotoxin components may include neurotoxin components that have modified amino acid side chains, as is well known in the art. Variants may also include fragments. An example of a variant neurotoxin component may comprise a variant light chain of a botulinum toxin having one or more amino acids substituted, modified, deleted and/or added. This variant light chain may have the same or better ability to prevent exocytosis, for example, the release of neurotransmitter vesicles. Additionally, the biological effect of a variant may be decreased compared to the parent chemical entity. For example, a variant light chain of a botulinum toxin type A having an amino acid sequence removed may have a shorter biological persistence than that of the parent (or native) botulinum toxin type A light chain.

"Fragment" means an amino acid or nucleotide sequence that comprises 1% or more of the parent amino acid or nucleotide sequence. For example, a fragment of botulinum toxin type A comprises 1% or more of the amino acid sequence of botulinum type A.

Embodiments of the invention include methods and compositions to prevent and treat infraorbital dark circles using botulinum toxins. Accordingly, methods of the invention deliver a neurotoxin to a tissue of an animal or a human subject. In one embodiment, the drug is delivered to the layer of the skin in which nerve terminals are found. For example, delivery is to the dermis layer. In another embodiment, delivery is to at least one layer of the skin and substantially to tissues beneath. For example, the administration to the dermis layer of the skin and to the subcutaneous layer. In another embodiment, delivery is to the skin and to muscle tissues beneath. In still another embodiment, delivery is substantially to the muscle tissue.

The location for administration of the botulinum toxin can be in the periocular region, inferior and superior to the lateral and medial canthus along the orbital rim including the lateral bridge of the nose. The botulinum toxin can be placed inside and outside of the orbital rim to enhance blood flow in these regions and thus lessen the appearance of infraorbital dark circles.

In embodiments, the composition can be administered locally, such as, for example, by injection, or topically, or the like. In embodiments utilizing injection administration, the injection can be performed with standard needles, or microneedles, or the like. In embodiments, compositions of the invention are injected needlelessly.

In one embodiment, the composition is administered to one or more layers of a skin where a nerve is located. In another embodiment, the neurotoxin is administered to a skin and substantially to a muscle tissue. In still another embodiment, the neurotoxin component is administered to a muscle tissue. Still further in accordance with embodiments of the present invention, the neurotoxin component may be a botulinum toxin type A, B, $C_1$, D, E, F, or G or a variant thereof. Still further in accordance with embodiments of the present invention, the neurotoxin component may comprise a targeting component, a therapeutic component and a translocation component. In one embodiment, the targeting component binds to a cell, for example, a nerve cell. In one embodiment the targeting component binds to a pre-synaptic nerve terminal. The pre-synaptic nerve terminal can belong to a cholinergic neuron. The targeting component may comprise, for example, a carboxyl end segment of a heavy chain of a butyricum toxin, a tetani toxin or a botulinum toxin type A, B, $C_1$, D, E, F, G or a variant thereof. In one embodiment, the therapeutic component substantially interferes with exocytosis from a cell, for example, interfering with the release of neurotransmitters from a neuron or its terminals.

In general, the amount of botulinum neurotoxins used for treatment will be determined by the age, gender, presenting condition and weight of the patient, in consideration of the potency of the presynaptic neurotoxin. The potency of a botulinum toxin is expressed as a multiple of the $LD_{50}$ value for a reference mammal. One "unit" of toxin is the amount of toxin that kills 50% of a group of mammals that were disease-free prior to inoculation with the toxin. For example, one unit of botulinum toxin is defined as the $LD_{50}$ upon intraperitoneal injection into female Swiss Webster mice weighing 18-20 grams each. One nanogram of the commercially available Botulinum toxin type A typically contains about 40 mouse units. The potency in humans of the Botulinum toxin type A product currently supplied by Allergan, Inc. as BOTOX® is estimated to be about $LD_{50}$=2,730 units.

Assuming an approximate potency of $LD_{50}$=2,730 units, the botulinum neurotoxin can be administered in a dose of up to about 1,000 units; however, dosages of as low as about 2.5 to 5 units will have therapeutic efficacy. Dosages between 2.5 or 5 units and as high as 250 units will be normally used, and in one embodiment, individual dosages will be of about 15-30 units. Typically, the botulinum neurotoxin will be administered as a composition at a dosage that is proportionally equivalent to a range of between 1 cc-5 cc/100 units, which translate to 100 units/cc-20 units/cc. Adjustment of these dosages depending on the greater or lesser potency of the botulinum neurotoxins and factors identified above should be easily determined by those of ordinary skill in the art.

In one embodiment, the dosage used will be the lowest one which is still therapeutically effective (i.e., the dosage which results in detection by the patient of a reduction in the occurrence and/or magnitude of the appearance of infraorbital circles experienced by the patient). The patient's sensitivity to, and tolerance of, the botulinum neurotoxin can be determined in the initial treatment by administering a low dosage at one site. Additional administrations of the same or different dosages can be provided as needed.

Administration can be repeated as necessary. As a general guideline, botulinum toxin type A administered into or near muscle tissue has been observed to produce flaccid paralysis at target site muscles for up to about 3 to 6 months. However, increased efficacy of the treatment using botulinum toxin type A is expected to happen when the toxin is administered according to the disclosed method at about 3 month intervals.

In one embodiment, commercially available BOTOX® can be reconstituted with sterile non-preserved saline prior to injection. Each vial of BOTOX® contains about 100 units or about 200 units of clostridium botulinum toxin type A purified neurotoxin complex. Dilutions will vary depending upon the commercial preparation.

In certain embodiments, the botulinum toxin can be administered in conjunction with another therapy, such as, for example, a pharmaceutical agent, or the like, or a surgical procedure, or the like. In certain embodiments the pharmaceutical agent can be, for example, an anti-inflammatory, or the like. In certain embodiments the surgical procedure can be, for example, insertion or injection or placement of a dermal filler such as, for example, collagen, or hyaluronic acid (HA), or the like. In certain embodiments the surgical procedure can be, for example, a fat transplant, such as an autologous fat transplant, or the like.

In certain embodiments the composition comprises a crosslinked HA component and an uncrosslinked HA component. The crosslinked HA component itself comprises a mixture of a first molecular weight HA material and a second, different molecular weight HA material. The first molecular weight HA material may have a relatively low molecular weight and the second HA molecular weight HA material may have a relatively high molecular weight. Generally, the crosslinked HA component includes more than 50%, for example, at least 70%, for example, about 90% by weight the low molecular weight HA.

In embodiments the uncrosslinked HA component is a relatively high molecular weight HA material, for example, a HA having a molecular weight of at least about 1.0 MDa, and may be present in the composition in an amount of less than about 10%, for example, less than 5.0%, for example, less than about 2.0%, for example, less than about 1.0%, for example, about 0.95% w/w.

The crosslinking agent may be any suitable crosslinking agent, but in a particular embodiment, the crosslinking agent is selected from the group consisting of 1,4-butanediol diglycidyl ether (BDDE), 1,4-bis(2,3-epoxypropoxy)butane, 1,4-bisglycidyloxybutane, 1,2-bis(2,3-epoxypropoxy)ethylene and 1-(2,3-epoxypropyl)-2,3-epoxycyclohexane, and 1,4-butanediol diglycidyl ether. In some embodiments, the compositions further comprise at least active agent, for example, an anesthetic agent combined with said crosslinked HA component.

In certain embodiments the crosslinked HA component has a total HA concentration of at least 10.0 mg/g. In certain specific embodiments, the crosslinked HA component has a total HA concentration of at least about 10.0 mg/g, for example, about 15.0 mg/g, about 17.0 mg/g, about 17.5 mg/g or about 20.0 mg/g, or about 25.0 mg/g.

Methods of making soft tissue filler compositions are also provided. In one embodiment, a method of making a soft tissue filler composition generally comprise the steps of providing a crosslinked hyaluronic acid (HA) gel comprising a mixture of a first molecular weight HA material and a second, different, for example, higher, molecular weight HA material, preparing a separate solution of an uncrosslinked hyaluronic acid of a relatively high molecular weight and combining the crosslinked gel with a small amount of the uncrosslinked solution. The compositions may include at least one anesthetic agent combined with said crosslinked HA component. The crosslinked HA component has a total HA concentration of at least 10 mg/g.

Embodiments of the invention can comprise an anesthetic. In embodiments of the invention including an anesthetic agent, the agent may comprise lidocaine. In a further embodiment, the amount of the anesthetic agent is present at a concentration between about 0.1% and about 5.0% by weight of the composition. In still another embodiment, the anesthetic agent is present at a concentration between about 0.2% and about 1.0% by weight of the composition. In one embodiment, the anesthetic agent is lidocaine and is present at a concentration of about 0.3% by weight of the composition.

In yet another embodiment, the composition has a complex viscosity of between about 50 Pa*s and about 450 Pa*s, for example, when measured at about 5 Hz with an rheometer using a cone/plate geometry (4 cm/2°) at 25° C.

In one embodiment, the HA component is a gel, for example, a cohesive, hydrated gel. In one embodiment, the HA component is a crosslinked HA gel having no greater than about 1% to about 10% uncrosslinked HA. Compositions of the invention may be administered to the skin. The skin may comprise an epidermis layer, a dermis layer and a hypodermis layer.

EXAMPLES

Example 1

Treatment of a Female Patient for Infraorbital Dark Circles

A female patient 37 years old wants to reduce the appearance of dark circles surrounding her upper and lower eyelids. She states that these dark circles make her appear angry, tired, and old. The patient explains to her physician that she uses makeup as a cover-up daily and places slices of cucumbers on her eyes and applies facial creams once per week. She is not satisfied with these treatments and would like assistance with this condition. A solution containing BOTOX® (ALLERGAN®, Inc) is reconstituted according to the manufacturer's instructions and three (3) Units are injected at four (4) sites just inside the orbital rim of each eye (as depicted in FIG. 1). These sites are chosen due to the patient's infraorbital dark circles covering a relatively small area and not reaching the orbital rim. Within two (2) weeks the dark circles have significantly improved. This effect lasts six (6) months until the patient requests re-treatment from her physician.

Example 2

Treatment of a Male Patient for Infraorbital Dark Circles

Figure 2:
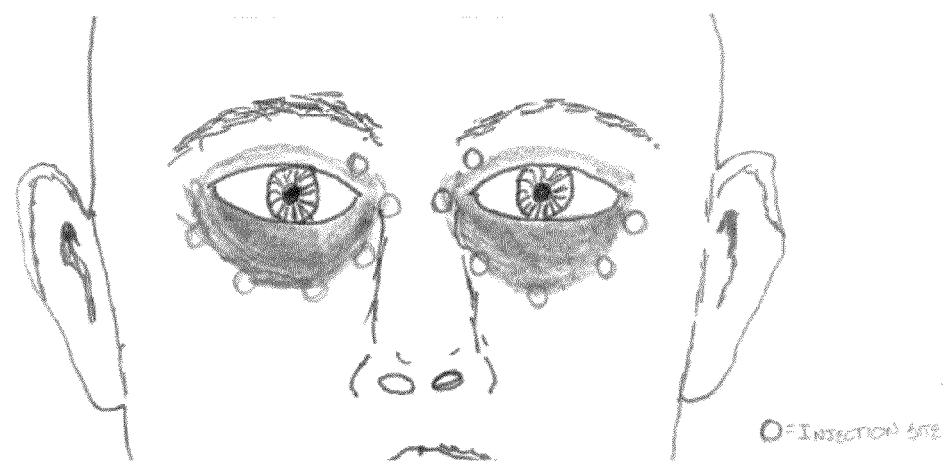
FIG. 2 depicts the injection protocol used in Example 2, wherein six (6) injection sites are employed inside and outside the orbital rim for each eye, beginning on the eye's outer edge and extending along the bottom edge toward and around the inner edge.

A male patient 50 years old presents to his physician's office requesting aesthetic enhancements including treatment for profuse dark circles surrounding his eyes. This appearance has had a negative impact on his social life and emotional state. He has not tried any treatments. A solution containing BOTOX® (ALLERGAN®, Inc) is reconstituted according to the manufacturer's instructions and four (4) Units are injected at six (6) sites inside and outside of the orbital rim of each eye (as depicted in FIG. 2). These sites are chosen due to the profuse infraorbital discoloration. The patient's condition improves within one (1) week and remains improved at month four (4). He reports improved self-esteem and confidence.

Example 3

Manufacture of a Low Molecular Weight Soft Filler/Botulinum Composition

90% of NaHA fibers or powder having a low molecular weight and 10% of NaHA fibers or powder having a high molecular weight, (ratio of high molecular weight to low molecular weight of 2:1) are hydrated in an alkaline solution, for example, an aqueous solution containing NaOH. The mixture is mixed at ambient temperature, about 23° C., to form a substantially homogenous, alkaline HA gel. A crosslinking agent, BDDE, is diluted in an aqueous solution and added to the alkaline HA gel. The mixture is homogenized for several minutes.

The resulting crosslinked HA gel mixture is then heated at about 50° C. for about 3 hours. The material is now a highly crosslinked HA/BDDE gel (aspect=solid gel). This crosslinked gel is then neutralized with a suitable acidic solution. The neutralized HA gel is then swollen in a phosphate buffer at a cold temperature, for example a temperature of about 5° C., to obtain a highly cohesive HA gel. In this specific example, the phosphate buffered saline solution contains water-for-injection (WFI), disodium hydrogen phosphate, and sodium dihydrogen phosphate. When neutralized and swollen, the water absorbed by the crosslinked HA component is in a weight ratio of at least 1:1, and without the gel breaking into pieces.

The swollen HA gel is then mechanical stirred and filled into dialysis membranes and dialyzed against a phosphate buffer. The HA gel is filled into dialysis membranes and dialyzed against a phosphate buffer for up to several days with regular changes of the bath, in order to remove the un-reacted crosslinker, to stabilize the pH close to neutrality (pH=7.2) and to ensure proper osmolarity of the HA gel. The osmolarity of the resulting HA gel is between about 200 mOsmol and about 400 mOsmol, most preferably about 300 mOsmol.

After dialysis, the resulting HA gel has a substantially neutral pH, preferably about 7.2.

Lidocaine chlorhydrate (lidocaine HCl) in powder form is first solubilized in WFI and filtered through a 0.2 μm filter. Dilute NaOH solution is added to the HA gel in order to reach a slightly basic pH (for example, a pH of between about 7.5 and about 8). The lidocaine HCl solution is then added to the slightly basic gel to reach a final desired concentration, for example, a concentration of about 0.3% (w/w). The resulting pH of the HA/lidocaine mixture is then about 7 and the HA concentration is about 24 mg/mL. Mechanical mixing is performed in order to obtain a proper homogeneity in a standard reactor equipped with an appropriate blender mechanism.

An amount of uncrosslinked HA gel is added to the HA/lidocaine gel mixture. Specifically, high molecular weight HA fibers are swollen in a phosphate buffer solution, in order to obtain a homogeneous viscoelastic gel. This uncrosslinked HA gel is then added to the crosslinked HA/lidocaine gel (for example, at about 1%, w/w). The resulting gel is then filled into Ready-to-Fill sterile syringes and autoclaved at sufficient temperatures and pressures for sterilization for at least about 1 minute.

After autoclaving, the final HA/lidocaine product is packaged and distributed to physicians. The autoclaved HA/lidocaine product has a viscosity, cohesivity, and extrusion force that are acceptable. No degradation of the HA/lidocaine gel product is found during testing of the product after the product has spent several months in storage.

Example 4

Treatment of a Male Patient for Infraorbital Dark Circles with a Filler/Botulinum Composition Combination A male patient 29 years old presents to his physician's office requesting aesthetic enhancements including treatment for profuse dark circles surrounding his eyes. This appearance has had a negative impact on his social life and emotional state. A solution containing BOTOX® (ALLERGAN®, Inc) is reconstituted according to the manufacturer's instructions and mixed with the dermal filler material described in Example 3. Four (4) Units are injected at six (6) sites inside and outside of the orbital rim of each eye (as depicted in FIG. 2). These sites are chosen due to the profuse infraorbital discoloration. The patient's condition improves within one (1) week and remains improved at month four (4). He reports improved self-esteem and confidence.

I claim:

1. A method for reducing the appearance of a dark infraorbital circle in a mammal in need thereof, comprising the step of administering a therapeutically effective amount of a botulinum toxin to the periocular region, including areas inferior and superior to the eye's inner edge and outer edge and the lateral bridge of the nose, thereby effecting reduction of the appearance of the dark circle in the mammal in need thereof.

2. The method of claim 1, wherein the botulinum toxin is administered by injection.

3. The method of claim 2, wherein the botulinum toxin is selected from the group consisting of botulinum toxin type A, B, $C_1$, D, E, F and G.

4. The method of claim 3, wherein the botulinum toxin is botulinum toxin type A.

5. The method of claim 1, wherein the botulinum injection is administered topically.

6. The method of claim 5, wherein the botulinum toxin is selected from the group consisting of botulinum toxin type A, B, $C_1$, D, E, F and G.

7. The method of claim 6, wherein the botulinum toxin is botulinum toxin type A.

* * * * *